United States Patent [19]
Dos Santos et al.

[11] Patent Number: 5,864,049
[45] Date of Patent: Jan. 26, 1999

[54] PROCESS FOR THE PREPARATION OF MONO- AND DICARBOXYLIC ACIDS FROM UNSATURATED FATTY ACIDS AND/OR THEIR DERIVATIVES

[75] Inventors: Emmanuel Dos Santos, Feyzin; Pascal Metivier, Sainte Foy Les Lyon, both of France

[73] Assignee: Rhone-Poulenc Chimie, Courbevoie Cedex, France

[21] Appl. No.: 935,546

[22] Filed: Sep. 23, 1997

Related U.S. Application Data

[63] Continuation of Ser. No. 528,840, Sep. 15, 1995, abandoned.

[30] Foreign Application Priority Data

Sep. 16, 1994 [FR] France ................................. 94 11050

[51] Int. Cl.$^6$ ................................................ C07C 51/16
[52] U.S. Cl. ........................... 554/138; 554/139; 554/132
[58] Field of Search ..................... 384/139, 132, 384/138

[56] References Cited

U.S. PATENT DOCUMENTS 2,773,095  12/1956  Englert et al. .
5,380,928   1/1995  Malek et al. .

FOREIGN PATENT DOCUMENTS 1 400 437   9/1965  France .
2 223 349  10/1974  France .

Primary Examiner—Samuel Barts
Assistant Examiner—Deborah D. Carr

[57] ABSTRACT

The present invention relates to a process for the preparation of carboxylic acids from unsaturated fatty acids and/or their derivatives.

The process of the invention is characterized in that it comprises the following stages:

a stage which consists in oxidizing an unsaturated fatty acid in the form of acid and/or of ester using hydrogen peroxide, in the presence of a metal oxide or of a carboxylic acid optionally used in combination with a ruthenium-based catalyst, a stage which consists in reacting the reaction mixture originating from the preceding stage with nitric acid in the presence of a vanadium-based catalyst, optionally used in combination with a cocatalyst, and then a stage of recovery of the mono- and dicarboxylic acids.

It is particularly well suited for the preparation of saturated mono- and dicarboxylic acids obtained from unsaturated fatty acids such as oleic acid or from oils and fats.

56 Claims, No Drawings

PROCESS FOR THE PREPARATION OF MONO- AND DICARBOXYLIC ACIDS FROM UNSATURATED FATTY ACIDS AND/OR THEIR DERIVATIVES

This application is a continuation of application Ser. No. 08/528,840, filed Sep. 15, 1995 now abandoned.

BACKGROUND OF THE INVENTION

1. Field of the Invention

The present invention relates to a process for the preparation of carboxylic acids from unsaturated fatty acids and/or their derivatives.

More precisely, the invention relates to a process for the preparation of monofunctional and difunctional aliphatic carboxylic acids from unsaturated fatty acids in the form of acid or of ester and more particularly in the form of triglyceride.

2. Description of the Prior Art

Various processes have been proposed for carrying out the preparation of carboxylic acids from unsaturated fatty acids.

A relatively old process described in U.S. Pat. No. 2,773,095 consists in performing the oxidation of the latter compounds by subjecting them to an oxidation with the aid of dilute nitric acid under pressure. The oxidation of oleic acid results in pelargonic acid and azelaic acid being obtained. However, the selectivity of the reaction conducted according to U.S. Pat. No. 2,773,095 is poor because an overoxidation is observed, resulting in the formation of lower monoacids and diacids.

Furthermore, it is known according to U.S. Pat. No. 2,865,937 to prepare mono- and dicarboxylic acids from unsaturated fatty acids, especially oleic acid, by subjecting the starting substrate to a scission by ozonolysis, followed by an oxidizing decomposition. A major disadvantage of this type of process is its prohibitive cost resulting from the use of ozone.

Another, equally costly, process is described in FR-A 2 101 729. An example of preparation mentions the oxidation of oleic acid with hydrogen peroxide, followed by hydrolysis with sulphuric acid, separation using solvent and another oxidation stage performed using a percarboxylic acid in the presence of metal ions. Besides the number of stages described, the high cost of the reactants engaged has to be noted.

None of these processes are satisfactory because they are difficult to transpose to an industrial scale, either because of poor reaction yields or for economic reasons.

The objective of the present invention is to provide a process enabling the abovementioned disadvantages to be avoided.

SUMMARY OF THE INVENTION

The process of the present invention includes the preparation of mono- and dicarboxylic acids from unsaturated fatty acids and/or their derivatives. The process comprises the following stages:
  oxidizing an unsaturated fatty acid in the form of acid and/or of ester using hydrogen peroxide, in the presence of a metal oxide or of a carboxylic acid optionally used in combination with a ruthenium-based catalyst,
  reacting the reaction mixture originating from the preceding stage with nitric acid in the presence of a vanadium-based catalyst, optionally used in combination with a cocatalyst, and then
  recovering the mono- and dicarboxylic acids.

The process of the invention comprises a first operation of controlled oxidation of the starting substrate, thus making it possible to limit the consumption of hydrogen peroxide leading to an intermediate product in which the double bonds are oxidized to an epoxy bridge and/or to two vicinal hydroxyl groups.

Without isolation of the intermediate product, a stage of scission and of oxidizing hydrolysis performed using nitric acid is linked into a sequence, thus making it possible to obtain the desired mono- and dicarboxylic acids.

The process of the invention is particularly advantageous because it makes it possible to obtain the acids with a good reaction selectivity.

In addition, it entails a reactant cost which is wholly compatible with industrial use.

Finally, another advantage, which is by no means a minor one, is that it can be applied not only with unsaturated fatty acids, for example oleic acid, but also by starting from unsaturated fatty acids in the form of triglycerides, and this makes it possible to start directly from oils or from fats that contain them.

The process of the invention thus makes it possible to make profitable use of oils, especially rapeseed and sunflower oils which may be available on the market in a large quantity.

DETAILED DESCRIPTION OF THE PREFERRED EMBODIMENTS OF THE INVENTION

The process of the invention applies to any fatty acid containing at least one double bond.

The fatty acid may be symbolized by the formula (I):

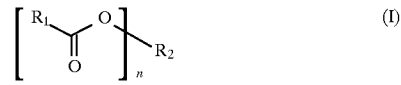

in which:
  n is a number equal to 1, 2 or 3,
  $R_1$ denotes a linear or branched alkenyl or alkadienyl radical containing from 4 to 40 carbon atoms,
  $R_2$ may make the following meanings:
    if n=1, $R_2$ denotes a hydrogen atom, or an alkyl radical, preferably containing from 1 to 6 carbon atoms, optionally carrying one or more hydroxyl groups,
    if n=2, $R_2$ denotes an alkylene or alkenylene radical, preferably containing from 1 to 6 carbon atoms, optionally carrying one or more hydroxyl groups,
    if n=3, $R_2$ denotes an alkyl radical containing 3 carbon atoms.

The compounds used preferably correspond to the formula (I) in which $R_1$ denotes an alkenyl radical containing from 6 to 22 carbon atoms and containing from 1 to 5 double bonds, preferably 1 to 3, and $R_2$ denotes a hydrogen atom or an alkyl radical containing from 1 to 4 carbon atoms optionally carrying from 1 to 2 hydroxyl groups where n=1, a diethylene or propylene radical optionally carrying a hydroxyl group where n=2, or a 1,2,3-propanetriyl radical where n=3.

Examples of unsaturated fatty acids which may be mentioned are the unsaturated fatty acids containing only one double bond, such as linderic acid, myristoleic acid, palmitoleic acid, oleic acid, petroselenic acid, doeglic acid, gadoleic acid and erucic acid, unsaturated fatty acids containing two double bonds, such as linoleic acid, unsaturated fatty acids containing three double bonds, such as linolenic acid, unsaturated fatty acids containing more than four double bonds, such as isanic acid, stearodonic acid, arachidonic acid and chypanodonic acid, and unsaturated fatty acids carrying a hydroxyl group, such as ricinoleic acid, and mixtures thereof.

Among the abovementioned acids the following fatty acids are preferably used: palmitoleic acid, oleic acid, petroselenic acid, erucic acid, linoleic acid, linolenic acid and ricinoleic acid.

A natural source of the fatty acids are oils and fats.

In fact, the process of the invention is particularly advantageous because it makes it possible to start from natural oils and fats, which are glycerol esters. They contain mixtures of fatty acid triglycerides generally mixed with saturated fatty acids.

Sources of animal origin which may be mentioned are, among others, sperm whale oil, dolphin oil, whale oil, seal oil, sardine oil, herring oil, dogfish oil, cod liver oil, neat's-foot oil and beef, pork, horse and mutton fats (tallows).

Examples of sources of vegetable oils which may be mentioned are, among others, rapeseed oil, sunflower oil, groundnut oil, olive oil, nut oil, corn oil, soya oil, linseed oil, hemp oil, grapeseed oil, copra oil, palm oil, cottonseed oil, babassu oil, jojoba oil, sesame oil and castor oil.

The oils mentioned below are used preferentially in the process of the invention: rapeseed oil, sunflower oil, soya oil, linseed oil and castor oil.

It is also possible to start from the esters corresponding to the said acids, in particular the methyl, ethyl and propyl esters, and more particular mention may be made of the products of methanolysis especially of the oils and more preferably of rapeseed oils.

In the following description of the present invention the term "unsaturated fatty acid" will be employed generically and will refer to both the unsaturated fatty acids strictly speaking, by themselves or mixed, and their ester or triglyceride form.

In accordance with the process of the invention the oxidation of the unsaturated substrate is performed with hydrogen peroxide.

The hydrogen peroxide used according to the invention may be in the form of an aqueous solution.

The concentration of the aqueous solution of hydrogen peroxide is generally at least 20% by weight of $H_2O_2$ and, preferably, between 20 and 70% by weight.

The quantity of hydrogen peroxide used is a function of the number of double bonds to be oxidized which are present in the starting substrate. A quantity equal to the stoichiometry or a slight excess ranging from 0 to 50%, preferably between 1 and 20%, is generally used.

The first stage of the process of the invention may be conducted according to various alternative forms which differ in what is used in combination with the hydrogen peroxide.

One embodiment of the invention consists in adding a carboxylic acid to the hydrogen peroxide, thus permitting the in-situ formation of a peracid.

The carboxylic acids liable to be used may be mono- or polycarboxylic. They are compounds which do not contain unsaturations.

They correspond more particularly to the following general formula (II):

$$R_3\text{—COOH} \qquad (II),$$

in the said formula (II), $R_3$ denotes a hydrocarbon radical containing from 1 to 22 carbon atoms, which may be a linear or branched, saturated acyclic aliphatic radical or a monocyclic or polycyclic saturated cycloaliphatic radical.

The said radical $R_3$ may carry another COOH functional group. It may also carry other substituents, for example alkoxy or halogen, provided that they do not interfere in the reaction.

$R_3$ denotes more particularly a linear or branched alkyl radical containing from 1 to 22 carbon atoms or a cycloalkyl radical containing from 5 to 7 carbon atoms.

Examples which may be mentioned of carboxylic acids liable to be used in the process of the invention are aliphatic monocarboxylic acids such as formic acid, acetic acid, propionic acid, butyric acid, valeric acid and hexanoic acid, aliphatic dicarboxylic acids such as succinic acid and adipic acid, and cycloaliphatic acids such as cyclopentanecarboxylic acid and cyclohexanecarboxylic acid.

Among the abovementioned carboxylic acids those preferably used are saturated aliphatic carboxylic acids, preferably formic acid or acetic acid.

It is also advantageous to use a carboxylic acid which is recovered in the products formed in the course of the process of the invention and pelargonic acid, azelaic acid and stearic acid may be mentioned more particularly.

It will not constitute a departure from the scope of the present invention to use either a percarboxylic acid directly instead of preparing it in situ, or a precursor of a carboxylic acid which would produce the latter in the oxidizing reaction conditions.

The quantity of carboxylic acid used may vary within wide limits. It may range from a catalytic quantity to a stoichiometric quantity.

More precisely, the molar ratio of hydrogen peroxide to the carboxylic acid varies between 10 and 500%, preferably between 10 and 40%.

According to a modified alternative form, it is also possible according to the invention to perform the oxidation of the unsaturated fatty acid, using hydrogen peroxide, in the presence of carboxylic acid and of a ruthenium-based catalyst.

Any ruthenium compound may be used as catalyst.

Examples which may be mentioned of compounds liable to be used as catalysts of the invention are, among others, ruthenium(III) chloride, ruthenium(IV) chloride, ruthenium pentafluoride, ruthenium(II) oxide, ruthenium(IV) oxide, ammoniated ruthenium oxychloride $Ru_2(OH)_2 Cl_4.7NH_3.5H_2O$ and ruthenium acetate.

Ruthenium(III) chloride is preferably chosen as ruthenium-based catalyst.

The quantity of ruthenium-based catalyst which is used, expressed as the weight ratio of hydrogen peroxide to the catalyst, may be advantageously between 1 and 35%, preferably between 3 and 10%.

Another alternative form of embodiment of the first stage of controlled oxidation involved in the process of the invention consists in performing the oxidation of the unsaturated fatty acid with hydrogen peroxide in the presence of a catalyst based on a metal of group VIa of the Periodic Classification of the elements.

For the definition of the elements, reference is made below to the Periodic Classification of the elements published in the Bulletin de la Société Chimique de France, No. 1 (1966).

A tungsten- and/or molybdenum-based catalyst is preferably used.

The catalyst is preferably chosen from tungstic acid, phosphotungstic acid, molybdic acid and phosphomolybdic acid.

It is therefore preferably in acidic form. It is possible to start directly from the abovementioned compounds or else to form them in situ from their oxides or salts.

Examples of molybdenum-based catalysts which may be mentioned are especially:

- molybdenum halides, for example molybdenum hexafluoride, molybdenum tri-, tetra- or pentachloride and molybdenum di-, tri- or tetrabromide,
- molybdenum hydroxides $Mo(OH)_3$, $MoO(OH)_3$ or $Mo_2O_3.3H_2O$,
- molybdenum oxides such as molybdenum dioxide, trioxide, pentaoxide or sesquioxide,
- molybdenum oxyhalides such as molybdenum oxydifluoride or oxytetrafluoride, molybdenum oxydichloride, oxytrichloride, oxytetrachloride, oxypentachloride, molybdenum acid oxychloride and molybdenum oxydibromide,
- molybdenum metaphosphate,
- ammonium phosphomolybdate,
- ammonium molybdate.

Where the tungsten-containing catalyst is concerned, it is possible to start more particularly from:

- tungsten halides, for example tungsten hexafluoride, tungsten di-, tetra-, penta- or hexachloride and tungsten di-, penta- or hexabromide,
- tungsten oxides such as tungsten dioxide, trioxide, pentaoxide or sesquioxide,
- tungsten oxyhalides such as tungsten oxytetrafluoride, tungsten oxydichloride and oxytetrachloride and tungsten oxydibromide and oxytetrabromide,
- tungsten metaphosphate,
- ammonium tungstate,
- ammonium phosphotungstate.

The quantity of tungsten- and/or molybdenum-based catalyst used, expressed as the weight ratio of hydrogen peroxide to the catalyst, may be advantageously between 1 and 35%, preferably between 3 and 10%.

The formation of the catalysts in acid form takes place when starting from the abovementioned compounds, by addition of a small quantity of strong acid.

A strong acid refers, in the present invention, to an acid which has a pKa in water lower than −0.1 and preferably lower than −1.0.

The pKa is defined as the ionic dissociation constant of the acid/base pair when water is employed as solvent.

There may be mentioned more particularly the oxyacids, whether containing halogen or not, such as nitric acid, sulphuric acid, pyrosulphuric acid, phosphoric acid, polyphosphoric acids, perchloric acid, halosulphonic acids such as fluorosulphonic acid, chlorosulphonic acid or trifluoromethanesulphonic acid, methanesulphonic acid, ethanesulphonic acid, ethanedisulphonic acid, benzenesulphonic acid, benzenedisulphonic acids, toluenesulphonic acids, naphthalenesulphonic acids and naphthalenedisulphonic acids.

Nitric acid, sulphuric acid or phosphoric acid is chosen very particularly among these acids.

The quantity of strong acid which is used, expressed as the weight ratio of the strong acid to hydrogen peroxide, may be advantageously between 1 and 50%, preferably between 5 and 20%.

The first oxidation stage is performed at a temperature which is advantageously between 30° and 100° C., preferably between 60° C. and 100° C.

The process of the invention is generally carried out at atmospheric pressure, but it may also be carried out at pressures which are higher or lower than atmospheric pressure.

From a practical viewpoint, the process of the invention is easy to carry out. The various reactants are charged. There is no order of introduction to be followed, only it is preferred to add the hydrogen peroxide, using gradual, continuous or portionwise addition to a reaction mixture containing the substrate, the carboxylic acid and the catalysts if necessary.

At the end of reaction an intermediate product is obtained in which the double bonds are oxidized to an epoxy bridge and/or to two vicinal hydroxyl groups.

According to the process of the invention the intermediate product is not isolated and the next stage of scission and of oxidizing hydrolysis performed using nitric acid is directly linked into a sequence.

An aqueous solution of nitric acid which may be of any concentration and which may vary between 30% and 100% is used. However, a concentration of between 40% and 60% is preferred.

The nitric acid is used in a large excess. The quantity of nitric acid represents from 2 to 50 times the weight of the starting substrate and, more preferably, from 4 to 10 times.

It is preferable to include a generator of $NO^+$ in order to initiate the nitric oxidation. Accordingly, it is possible to start from nitrogen dioxide $NO_2$, from nitrogen trioxide $N_2O_3$, from nitrogen peroxide $N_2O_4$ or from nitrogen oxide NO. In the case where the said agent is gaseous in the reaction conditions, it is bubbled into the mixture.

It is also possible to make use of nitrous acid, of a nitrosylsulphate or nitrosylsulphuric acid or of a nitrous salt, preferably an alkali metal, and still more preferentially a sodium, salt.

The quantity of this agent may vary widely. It is advantageously between 0 and 5% of the weight of nitric acid, and preferably between 0 and 1%.

As mentioned above, the nitric acid is employed in the presence of a vanadium-based catalyst.

One of the compounds listed below may be employed, as catalyst:

- vanadium halides such as vanadium tri-, tetra- or pentafluoride, vanadium di-, tri- or tetrachloride or vanadium tribromide,
- vanadium oxides such as vanadium oxide, vanadium dioxide, vanadium sesquioxide or vanadium pentoxide,
- vanadium oxyhalides, in particular oxydi- or trifluoride, vanadium oxymono-, di- or trichloride and vanadium oxymono-, di- or tribromide,
- vanadium sulphate,
- vanadyl sulphate,
- alkali metal or ammonium vanadates in the ortho, meta or pyro form,
- vanadyl acetylacetonate.

This list does not constitute any limitation and it is also possible to make use of double salts containing vanadium.

Ammonium vanadates are preferably chosen as catalyst among the abovementioned compounds.

The quantity of vanadium-based catalyst used, expressed as the weight ratio of the catalyst, expressed as $HVO_3$, to nitric acid, is preferably between 0.001 and 1%, more preferably between 0.02 and 0.5%.

As mentioned above, a metallic cocatalyst, the role of which is to accelerate the speed of reaction, may be added during this nitric oxidation stage conducted in the presence of a vanadium-based catalyst.

Use is made of a cocatalyst based on a metal of group VIIa and VIII of the Periodic Classification of the elements, and catalysts based on manganese, iron, nickel, ruthenium and cobalt may be mentioned by way of preference.

Examples of compounds liable to be used as cocatalysts which may be mentioned are, among others, the oxides, hydroxides, nitrates, halides, oxyhalides, phosphates, pyrophosphates, carbonates, carboxylates and alcoholates of the various abovementioned metals.

The preferred salts are the following: iron(II) nitrate, iron(III) nitrate, nickel(II) nitrate, cobalt(II) nitrate, cobalt (III) nitrate, cobalt(II) acetate, manganese(II) carbonate and ruthenium(III) chloride.

The quantity or cocatalyst, expressed as the weight ratio of the cocatalyst to nitric acid, is preferably between 0.001 and 1%, preferably between 0.02 and 0.5%.

A preferred embodiment of the invention consists in performing this nitric oxidation stage in the presence of oxygen or a gas containing it.

It is thus possible, throughout the reaction, to regenerate nitric acid from nitrous acid.

This gas may be pure oxygen or a gas containing it, preferably air. In the case of pure oxygen, this may be bubbled into the reaction mixture at a flow rate, for example, of 0.1 to 50 litres/hour.

The quantity of oxygen to be used is not critical, provided that it is such that neither the feed gas nor a possible gas phase liable to appear in the reaction zone is in the region of explosive compositions, bearing in mind the other chosen reaction parameters or conditions. The quantity of oxygen may be in excess or in deficiency in relation to the stoichiometry of the reaction, in respect of the substrate to be oxidized.

It is generally determined as a function of the number of double bonds to be oxidized. It is from 1 to 2 times the stoichiometric quantity when the starting substrate is an unsaturated fatty acid and from 5 to 8 times stoichiometric quantity when the raw material is an oil or a fat.

The pressure of oxygen or of the reaction air varies between 1 and 10 bar.

The process of the invention may be conducted at atmospheric pressure.

In this second stage the reaction temperature is chosen preferably between 40° C. and 100° C. and more preferably between 60° and 90° C.

As previously, the reaction is advantageously conducted at atmospheric pressure.

The invention is easy to carry out in practice.

According to a preferred method the catalyst and optionally the cocatalysts are placed in the nitric acid solution, which is then introduced into the reaction mixture originating from the preceding stage.

The gas stream containing oxygen is then bubbled through.

At the end of reaction the reaction mixture is two-phase.

The aqueous phase contains the nitric acid, the various catalysts, cocatalysts and the carboxylic acids which are predominantly the saturated dicarboxylic acids.

The organic phase contains essentially the saturated monocarboxylic fatty acids formed during the reaction and possibly those present initially, as well as the unsaturated fatty acids which have not reacted.

It should he noted that the process of the invention has the advantage of not degrading the saturated fatty acids which may be present in the starting substrate, especially in the case of oils and fats.

The separation of the aqueous and organic phases is undertaken preferably by settling while hot.

One or more washing operations of the organic phase are preferably performed with water in order to recover any saturated dicarboxylic fatty acids remaining in the organic phase. The aqueous washings may be combined with the aqueous phase obtained in the separation of the organic and aqueous phases.

The aqueous phase containing the saturated dicarboxylic fatty acids is cooled by returning the temperature to the ambient temperature.

The carboxylic acids crystallize and are recovered by following conventional solid/liquid separation techniques, preferably by filtration.

The separation may be optionally followed by one or more washing operation with water.

Furthermore, the organic phase is treated in order to remove the organic solvent by distillation.

The monocarboxylic acids are isolated from the organic phase by following conventional liquid/liquid separation techniques, preferably distillation.

The aqueous phase which contains the nitric acid and the catalysts and cocatalysts may be advantageously recycled after evaporation of the excess water, in order to obtain an adequate concentration of nitric acid.

The process of the invention is perfectly suitable for the preparation of pelargonic acid and azelaic acid, which are obtained from oleic acid and rapeseed and sunflower oils.

Examples of practical implementation of the invention are given below.

The examples which follow illustrate the invention without, however, limiting it.

The yields mentioned in the examples correspond to the following definition:

selectivity for azelaic acid: CY $$CY = \frac{\text{number of moles of azelaic acid which are formed}}{\text{number of moles of azelaic + suberic + pimelic acid which are formed}}$$

selectivity for pelargonic acid: CY $$CY = \frac{\text{number of moles of pelargonic acid which are formed}}{\text{number of moles of pelargonic + caprylic + heptanoic acids formed}}$$

EXAMPLE 1

In this example the oxidative scission of "oleic" sunflower oil is performed in the presence of formic acid and sulfuric acid.

828 mg of "oleic" sunflower oil are charged into a stirred reactor fitted with a condenser and a temperature probe.

The fatty acids composition of this sunflower oil is the following:

palmitic acid: 4.6% stearic acid: 4.8% oleic acid: 77.8% linoleic acid: 12.8%

413 mg of an aqueous solution of 30% strength aqueous hydrogen peroxide, that is 3.64 mmol, 5 g of formic acid and 250 mg of 96% sulphuric acid are added.

The reaction mixture is kept at 45° C. for 2 hours and then at 80° C. for 4 hours.

A reaction mixture based on nitric acid and made up of 13.2 ml of a 49% strength aqueous solution of nitric acid, 106 mg of ammonium metavanadate and 50 mg of sodium nitrite is then added slowly to this reaction mixture. The reaction mixture is then kept at 75° C. for 6 hours.

At the end of reaction the reaction mixture is cooled.

The pH is then brought to 2.4 by adding an aqueous solution of sodium hydroxide at a concentration of 36%.

The mixture is then made up to 500 ml and determined by capillary electrophoresis.

The results obtained are the following:
pelargonic acid: 236 mg
caprylic acid: 42 mg
heptanoic acid: 11 mg
azelaic acid: 117 mg
suberic acid: 13 mg
pimelic acid: 12 mg
The selectivity for azelaic acid is 82%.
The selectivity for pelargonic acid is 82%.

EXAMPLE 2

In this example the oxidative scission of "oleic" rapeseed oil is performed in the presence of formic acid and sulfuric acid.

830 mg of "oleic" rapeseed oil are charged into a stirred reactor fitted with a condenser and a temperature probe.

The fatty acids composition of this rapeseed oil is the following:
palmitic acid: 3.2%
stearic acid: 2%
oleic acid: 86.8%
linoleic acid: 2.3%
linolenic acid: 4.2%
gadoleic acid: 1.5%

430 mg of an aqueous solution of 30% strength aqueous hydrogen peroxide, that is 3.79 mmol, 5 g of formic acid and 250 mg of 96% sulphuric acid are added.

The reaction mixture is kept at 45° C. for 2 hours and then at 80° C. for 4 hours.

A reaction mixture based on nitric acid and made up of 13.2 ml of a 49% strength aqueous solution of nitric acid, 106 mg of ammonium metavanadate and 50 mg of sodium nitrite is then added slowly to this reaction mixture. The reaction mixture is then kept at 75° C. for 6 hours and then at 90° C. for 2 hours.

At the end of reaction the reaction mixture is cooled.

The pH is then brought to 2.4 by adding a 36% strength aqueous solution of sodium hydroxide.

The mixture is then made up to 500 ml and analysed by capillary electrophoresis.

The results obtained are the following:
pelargonic acid: 244 mg
caprylic acid: 45 mg
heptanoic acid: 13 mg
azelaic acid: 212 mg
suberic acid: 24 mg
pimelic acid: 18 mg
The selectivity for azelaic acid is 82%.
The selectivity for pelargonic acid is 79%.

EXAMPLE 3

In this example the oxidative scission of oleic acid is performed in the presence of formic acid.

867 mg of oleic acid (3.07 mmol) and 5 g of formic acid are charged into a 50-ml three-necked round bottom flask fitted with a mechanical stirrer, a thermometer and a reflux device.

797 mg of an aqueous solution of 30% strength aqueous hydrogen peroxide (7 mmol) are then added and the reaction mixture is heated to 40° C. for 2 hours.

A mixture containing 39 g of a 49% strength aqueous solution of nitric acid, 222 mg of ammonium metavanadate and 100 mg of sodium nitrite is then added directly to the reaction mixture. The reaction mixture is then kept at 60° C. for 6 hours.

The reaction mixture is then cooled, neutralized to pH=2.3 with a 36% strength aqueous solution of sodium hydroxide, diluted to 1 litre and analysed by capillary electrophoresis.

The results obtained are the following:
pelargonic acid: 247 mg
caprylic acid: 15 mg
heptanoic acid: 11 mg
azelaic acid: 284 mg
suberic acid: 24 mg
pimelic acid: 4 mg
The selectivity for pelargonic acid is 90%.
The selectivity for azelaic acid is 90%.

EXAMPLE 4

In this example the oxidative scission of erucic acid is performed in the presence of formic acid.

1.21 g of erucic acid (3.57 mmol), 0.36 g of formic acid and 0.8 g of 30% strength aqueous hydrogen peroxide (7.05 mmol) are charged into a stirred reactor fitted with a condenser and a temperature probe; the reaction mixture is then heated to 80° C. for 7 h.

13.4 g of a 55% strength aqueous solution of nitric acid, 70 mg of sodium nitrite and 133 mg of ammonium metavanadate are then added directly to the reaction mixture. The reaction mixture is then kept at 61° C. for 5 h 30 min.

The reaction mixture is then cooled, and neutralized to pH=2.3 with a 36% strength aqueous sodium hydroxide solution. The reaction mixture is then esterified and analysed by gas phase chromatography.

The results obtained are the following:
dimethyl brassylate: 465 mg
dimethyl dodecanedioate: 109 mg
dimethyl suberate: 1 mg
methyl pelargonate: 291 mg
methyl caprylate: 52 mg
methyl heptanoate: 2 mg
The selectivity for brassylic acid is 80%.
The selectivity for pelargonic acid is 83%.

EXAMPLE 5

In this example the oxidative scission of petroselenic acid is performed in the presence of formic acid.

0.99 g of petroselenic acid (3.51 mmol), 0.37 g of formic acid and 0.8 g of 30% strength aqueous hydrogen peroxide (7.05 mmol) are charged into a stirred reactor fitted with a condenser and a temperature probe; the reaction mixture is then heated to 80° C. for 7 h.

13.4 g of a 55% strength aqueous solution of nitric acid, 70 g of sodium nitrite and 133 mg of ammonium metavanadate are then added directly to the reaction mixture. The reaction mixture is then kept at 61° C. for 5 h 30 min. The react on mixture is then cooled, and neutralized to pH=2.3 with a 36% strength aqueous sodium hydroxide solution. The reaction mixture is then esterified and analysed by gas phase chromatography.

The results obtained are the following:
dimethyl adipate: 287 mg
dimethyl glutarate: 40 mg
methyl laurate: 400 mg
methyl undecanoate: 65 mg
methyl decanoate: 4 mg
The selectivity for adipic acid is 80%.
The selectivity for lauric acid is 78%.

EXAMPLE 6

In this example the oxidative scission of methyl oleate is performed in the presence of formic acid.

1.049 g of methyl oleate (3.54 mmol), 0.36 g of formic acid and 0.8 g of 30% strength aqueous hydrogen peroxide (7.05 mmol) are charged into a stirred reactor fitted with a condenser and a temperature probe; the reaction mixture is then heated to 80° C. for 7 h.

13.4 g of a 55% strength aqueous solution of nitric acid, 70 mg of sodium nitrite and 133 mg of ammonium metavanadate are then added directly to the reaction mixture. The reaction mixture is then kept at 61° C. for 5 h 30 min. The reaction mixture is then cooled, and neutralized to pH=2.3 with a 36% strength aqueous sodium hydroxide solution. The reaction mixture is then esterified and analysed by gas phase chromatography.

The results obtained are the following:
dimethyl azelate: 495 mg
dimethyl suberate: 51 mg
dimethyl pimelate: 4 mg
methyl pelargonate: 384 mg
methyl caprylate: 39 mg
methyl heptanoate: 5 mg
The selectivity for azelaic acid is 89%.
The selectivity for pelargonic acid is 89%.

EXAMPLE 7

In this example the oxidative scission of oleic acid is performed in the presence of hydrogen peroxide alone.

1.01 g of oleic acid (3.59 mmol) and 0.8 g of 30% strength aqueous hydrogen peroxide (7.05 mmol) are charged into a stirred reactor fitted with a condenser and a temperature probe; the reaction mixture is then heated to 80° C. for 7 h.

13.4 g of a 55% strength aqueous solution of nitric acid, 70 mg of sodium nitrite and 133 mg of ammonium metavanadate are then added directly to the reaction mixture. The reaction mixture is then kept at 61° C. for 5 h. The reaction mixture is then cooled and neutralized to pH=2.3 with a 36% strength aqueous sodium hydroxide solution. The reaction mixture is then esterified and analysed by gas phase chromatography.

The results obtained are the following:
dimethyl azelate: 76 mg
dimethyl suberate: 45 mg
dimethyl pimelate: 8 mg
dimethyl adipate: 24 mg
methyl pelargonate: 119 mg
methyl caprylate: 41 mg
methyl heptanoate: 6 mg
The selectivity for azelaic acid is 50%.
The selectivity for pelargonic acid is 68%.

EXAMPLE 8

In this example the oxidative scission of oleic acid is performed in the presence of sulfuric acid.

1.01 g of oleic acid (3.59 mmol), 0.12 of 98% strength sulphuric acid and 0.8 g of 30% strength aqueous hydrogen peroxide (7.05 mmol) are charged into a stirred reactor fitted with a condenser and a temperature probe; the reaction mixture is then heated to 80° C. for 7 h.

13.4 g of a 55% strength aqueous solution of nitric acid, 70 mg of sodium nitrite and 133 mg of ammonium metavanadate are then added directly to the reaction mixture. The reaction mixture is then kept at 61° C. for 5 h. The reaction mixture is then cooled and neutralized to pH=2.3 with a 36% strength aqueous sodium hydroxide solution. The reaction mixture is then esterified and analysed by gas phase chromatography.

The results obtained are the following:
dimethyl azelate: 316 mg
dimethyl suberate: 136 mg
dimethyl pimelate: 13 mg
dimethyl adipate: 6 mg
methyl pelargonate: 238 mg
methyl caprylate: 91 mg
methyl heptanoate: 7 mg
The selectivity for azelaic acid is 71%.
The selectivity for pelargonic acid is 60%.

EXAMPLE 9

In this example the oxidative scission of oleic acid is performed in the presence of tungstic acid.

1.0 g of oleic acid (3.54 mmol), 0.206 g of tungstic acid and 0.8 g of 30% strength aqueous hydrogen peroxide (7.05 mmol) are charged into a stirred reactor fitted with a condenser and a temperature probe; the reaction mixture is then heated to 80° C. for 5 h.

13.4 g of a 55% strength aqueous solution of nitric acid, 70 mg of sodium nitrite and 133 mg of ammonium metavanadate are then added directly to the reaction mixture. The reaction mixture is then kept at 61° C. for 6 h.

The reaction mixture is then cooled and neutralized to pH=2.8 with a 36% strength aqueous sodium hydroxide solution. The reaction mixture is then esterified and analysed by gas phase chromatography.

The results obtained are the following:
dimethyl azelate: 544 mg
dimethyl suberate: 82 mg
dimethyl pimelate: 8 mg
dimethyl adipate: 5 mg
methyl pelargonate: 416 mg
methyl caprylate: 58 mg
methyl heptanoate: 4 mg
The selectivity for azelaic acid is 84%.
The selectivity for pelargonic acid is 86%.

I claim:

1. A process for the preparation of mono- or dicarboxylic acids from unsaturated fatty acids or their ester derivatives, said process comprising:

(a) oxidizing an unsaturated fatty acid or its ester derivative with hydrogen peroxide in the presence of a least one organic or metallic catalyst, optionally in the presence of a ruthenium-based catalyst, to afford a reaction mixture in which the double bonds in the starting material have been converted to epoxy bridges or to vicinal hydroxyl groups;

(b) reacting the reaction mixture obtained in step (a) above with nitric acid in the presence of a vanadium-based catalyst, optionally in the presence of a co-catalyst, to afford the corresponding mono- or dicarboxylic acids; and then (c) recovering the mono- or dicarboxylic acids.

2. A process according to claim 1, wherein the at least one organic or metallic catalyst used in step (a) comprises a metal oxide.

3. A process according to claim 1, wherein the at least one organic or metallic catalyst used in step (a) comprises a carboxylic acid.

4. A process according to claim 1, wherein the ester derivative comprises triglyceride esters.

5. A process for the preparation of mono- or dicarboxylic acids from unsaturated fatty acids or their ester derivatives, said process comprising:

(a) oxidizing an unsaturated fatty acid or its ester derivative with hydrogen peroxide and an organic acid or a metallic catalyst, optionally in the presence of a ruthenium-based catalyst, at a temperature of from about 60° C. to about 100° C., to afford a reaction mixture in which the double bonds in the starting material have been converted to epoxy bridges or to vicinal hydroxyl groups;

(b) reacting the reaction mixture obtained in step (a) above with nitric acid in the presence of a vanadium-based catalyst, optionally in the presence of a co-catalyst, to afford the corresponding mono- or dicarboxylic acids, and then (c) recovering the mono- or dicarboxylic acids.

6. A process according to claim 5, wherein the organic acid is used in a stoichiometric amount.

7. A process according to claim 5, wherein the organic acid is used in a catalytic amount.

8. A process according to claim 5, wherein the organic acid is a carboxylic acid.

9. A process according to claim 5, wherein the metallic catalyst is a metal oxide.

10. A process according to claim 5, wherein the unsaturated fatty acid, in acid or ester form, comprises triglyceride esters.

11. A method for preparing mono- or dicarboxylic acids comprising:

(a) forming a reaction mixture by oxidizing an unsaturated fatty acid or its ester derivative with hydrogen peroxide in the presence of a metal oxide;

(b) reacting the reaction mixture with nitric acid in the presence of a vanadium based catalyst; and then (c) recovering said mono- or dicarboxylic acid from said reaction mixture.

12. The method according to claim 11 wherein said unsaturated fatty acid or said ester derivative corresponds to the formula (I):

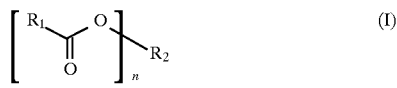

in which n=1, 2 or 3; $R_1$ denotes a linear or branched alkenyl or alkadienyl radical; and $R_2$ denotes a hydrogen atom, an alkyl radical, an alkylene radical or an alkenylene radical.

13. The method according to claim 12, wherein n=1 and $R_2$ denotes a hydrogen atom or an alkyl radical.

14. The method according to claim 12, wherein n=2 and $R_2$ denotes an alkylene or alkenylene radical.

15. The method according to claim 12, wherein n=3 and $R_2$ denotes an alkyl radical.

16. The method according to claim 12, wherein $R_1$ denotes an alkenyl radical containing 6 to 22 carbon atoms and 1 to 5 double bonds, and $R_2$ denotes a hydrogen atom or an alkyl radical containing from 1 to 4 carbon atoms.

17. The method according to claim 12, wherein $R_2$ is an alkyl radical possessing at least one hydroxyl group.

18. The method according to claim 12, wherein said unsaturated fatty acid or said ester derivative contains one, two or three double bonds.

19. The method according to claim 18, wherein said unsaturated fatty acid is linderic acid, myristoleic acid, palmitoleic acid, oleic acid, petroselenic acid, doeglic acid, gadoleic acid, erucic acid, linoleic acid, linolenic acid, isanic acid, stearodonic acid, arachidonic acid or chypanodonic acid, or said ester derivative is an ester derivative of linderic acid, myristoleic acid, palmitoleic acid, oleic acid, petroselenic acid, doeglic acid, gadoleic acid, erucic acid, linoleic acid, linolenic acid, isanic acid, stearodonic acid, arachidonic acid.

20. The method according to claim 12, wherein said unsaturated fatty acid contains at least one hydroxyl group.

21. The method according to claim 20, wherein said unsaturated fatty acid is ricinoleic acid or said ester derivative is an ester derivative of ricinoleic acid.

22. The method according to claim 12, wherein said unsaturated fatty acid or said ester derivative is an oil or fat of animal origin.

23. The method according to claim 22, wherein said unsaturated fatty acid is sperm whale oil, dolphin oil, whale oil, seal oil, sardine oil, herring oil, dogfish oil, cod liver oil, neat's-foot oil, beef fat, pork fat, horse fat or mutton fat, or said ester derivative is an ester derivative of sperm whale oil, dolphin oil, whale oil, seal oil, sardine oil, herring oil, dogfish oil, cod liver oil, neat's-foot oil, beef fat, pork fat, horse fat or mutton fat.

24. The method according to claim 12, wherein said unsaturated fatty acid or said ester derivative is an oil or fat of plant origin.

25. The method according to claim 24, wherein said unsaturated fatty acid is rapeseed oil, sunflower oil, groundnut oil, olive oil, nut oil, corn oil, soya oil, linseed oil, hemp oil, grapeseed oil, copra oil, palm oil, cottonseed oil, babassu oil, jojoba oil, sesame oil or castor oil, or said ester derivative is an ester derivative of rapeseed oil, sunflower oil, groundnut oil, olive oil, nut oil, corn oil, soya oil, linseed oil, hemp oil, grapeseed oil, copra oil, palm oil, cottonseed oil, babassu oil, jojoba oil, sesame oil or castor oil.

26. The method according to claim 12, wherein said unsaturated fatty acid is palmitoleic acid, oleic acid, petroselenic acid, erucic acid, linoleic acid, linolenic acid, ricinoleic acid, rapeseed oil, sunflower oil, soya oil, linseed oil or castor oil, or said ester derivative is an ester derivative of palmitoleic acid, oleic acid, petroselenic acid, erucic acid, linoleic acid, linolenic acid, ricinoleic acid, rapeseed oil, sunflower oil, soya oil, linseed oil or castor oil.

27. The method according to claim 11, wherein said hydrogen peroxide is present in at least a stoichiometric amount.

28. The process according to claim 27, wherein said hydrogen peroxide is present in an amount less than a 50% stoichiometric excess.

29. The process according to claim 28, wherein said hydrogen peroxide is present in a stoichiometric excess of between 1% and 20%.

30. The process according to claim 11, wherein said hydrogen peroxide is used in combination with a carboxylic acid.

31. The process according to claim 30, wherein the carboxylic acid corresponds to the general formula (II):

wherein R₃ denotes a hydrocarbon radical containing from 1 to 22 carbon atoms.

32. The process according to claim 30, wherein the carboxylic acid is a saturated aliphatic carboxylic acid.

33. The process according to claim 30, wherein the carboxylic acid is formic acid or acetic acid or an acid formed in the course of the reaction.

34. The process according to claim 30, wherein the carboxylic acid is pelargonic acid, azelaic acid or stearic acid.

35. The process according to claim 30, wherein the molar ratio of hydrogen peroxide to carboxylic acid is in a range from 10 to 500%.

36. The process according to claim 35, wherein the molar ratio of hydrogen peroxide to carboxylic acid is in a range from 10 to 40%.

37. The process according to claim 11, wherein a ruthenium-based catalyst is added.

38. The process according to claim 37, wherein the ruthenium-based catalyst is ruthenium(III)chloride, ruthenium (IV) chloride, ruthenium pentafluoride, ruthenium (II) oxide, ruthenium (IV) oxide, ammoniated ruthenium oxychloride $Ru_2(OH)_2Cl_4 \cdot 7NH_3 \cdot 5H_2O$ or ruthenium acetate.

39. The process according to claim 37, wherein the quantity of the ruthenium-based catalyst, expressed as the weight ratio of hydrogen peroxide to the catalyst, is in a range from 1 to 35%.

40. The process according to claim 11, wherein the hydrogen peroxide is used in combination with a catalyst based on a metal of group VIa of the Periodic Classification of the elements.

41. The process according to claim 40, wherein the catalyst is tungstic acid, phosphotungstic acid, molybdic acid, phosphomolybdic acid or their precursors.

42. The process according to claim 40, wherein the quantity of catalyst based on a metal of Group VIa, expressed as the weight ratio of hydrogen peroxide to the catalyst, is in a range from 1 to 35%.

43. The process according to claim 40, wherein a strong acid is added.

44. The process according to claim 43, wherein said strong acid is nitric acid, sulphuric acid or phosphoric acid.

45. The process according to claim 11, wherein the oxidizing temperature is in a range from 30° to 100° C.

46. The process according to claim 11, wherein the quantity of nitric acid used represents from 2 to 50 times the weight of said fatty acid.

47. The process according to claim 46, wherein a source of $NO^+$ is added.

48. The process according to claim 47, wherein said source of $NO^+$ is nitrogen dioxide, nitrogen trioxide, nitrogen peroxide, nitrogen oxide, nitrous acid, a nitrosylsulphate or nitrosylsulphuric acid or a nitrous salt.

49. The process according to claim 11, wherein the vanadium-based catalyst is a vanadium halide, oxide, oxyhalide, sulphate, alkali metal or ammonium vanadate or vanadyl acetylacetonate.

50. The process according to claim 11, wherein the quantity of vanadium-based catalyst used, expressed as $HVO_3$, is in a range from 0.001 to 1%.

51. The process according to claim 11, wherein a cocatalyst for the vanadium-based catalyst is added.

52. The process according to claim 51, wherein said cocatalyst is based on a metal of group VIIa or VIII of the Periodic Classification.

53. The process according to claim 52, wherein said cocatalyst is based on manganese, iron, nickel, ruthenium and/or cobalt.

54. The process according to claim 11, wherein said reacting is performed in the presence of oxygen or a gas containing oxygen.

55. The process according to claim 11, wherein the reaction temperature for reacting the reaction mixture with nitric acid is between 40° C. and 100° C.

56. The process according to claim 11, wherein a two-phase mixture is obtained comprising an aqueous phase including saturated dicarboxylic fatty acids, nitric acid, and catalysts; and an organic phase including saturated monocarboxylic fatty acids formed in the course of the reaction.

* * * * *